United States Patent [19]
Jansen et al.

[11] Patent Number: 6,002,047
[45] Date of Patent: Dec. 14, 1999

[54] CATALYTIC HYDROGENATION USING AMORPHOUS METAL ALLOY AND A SOLVENT UNDER NEAR-CRITICAL OR SUPER-CRITICAL CONDITIONS

[75] Inventors: Michael Jansen, Bartenheim, France; Claus Rehren, Aschaffenburg, Germany

[73] Assignee: Roche Vitamins Inc., Nutley, N.J.

[21] Appl. No.: 08/959,221

[22] Filed: Oct. 28, 1997

[30] Foreign Application Priority Data

Nov. 11, 1996 [EP] European Pat. Off. .............. 96118038

[51] Int. Cl.$^6$ ................................................... C07C 45/45
[52] U.S. Cl. ...................... 568/395; 568/396; 568/388; 568/404; 568/903
[58] Field of Search .................... 568/903, 388, 568/395, 396, 404; 420/4, 86, 458, 463, 469, 490, 441

[56] References Cited

U.S. PATENT DOCUMENTS

| | | | |
|---|---|---|---|
| 4,645,849 | 2/1987 | Lewis | 556/16 |
| 4,727,202 | 2/1988 | Franzen et al. | 585/259 |
| 4,735,789 | 4/1988 | Franzen et al. | 423/362 |
| 4,918,254 | 4/1990 | Diefenbach et al. | 585/328 |
| 4,939,296 | 7/1990 | Franzen et al. | 562/415 |

FOREIGN PATENT DOCUMENTS

| | | |
|---|---|---|
| 2182782 | 8/1995 | Canada . |
| 173 088 | 3/1986 | European Pat. Off. . |
| 44 05 029 | 3/1986 | Germany . |

OTHER PUBLICATIONS von Rohr et al., Elsevier Science B. V., pp. 191–197 (1996).
Molnar et al., Journal of Catalysis, 101:67–72 (1986).
Gasser et al., Applied Catalysis, 48:279–294 (1989).
A. Baiker, "Glassy Metals in Catalysis", Topics in Appl. Physics, vol. 72, Ed. H. Beck and H.J. Güntherodt, Springer Verlag 1994.

*Primary Examiner*—Shailendra Kumar
*Assistant Examiner*—S. Padmanabhan
*Attorney, Agent, or Firm*—Mark E. Waddell; Stephen M. Haracz; Bryan Cave LLP

[57] ABSTRACT

The present invention is concerned with a process for the catalytic hydrogenation of organic compounds on a catalyst of amorphous metal alloys and in a solvent, with the hydrogenation being carried out under near-critical or super-critical conditions of the solvent. The amorphous metal alloys can be produced by the shock cooling of alloy melts having eutectic solidification points. By hydrogenation at hydrogen partial pressures between 5 and 400 bar there is obtained outstanding space-time yields with high long-term stability of the catalytic activity.

21 Claims, 1 Drawing Sheet

CATALYTIC HYDROGENATION USING AMORPHOUS METAL ALLOY AND A SOLVENT UNDER NEAR-CRITICAL OR SUPER-CRITICAL CONDITIONS

BACKGROUND OF THE INVENTION

1. Field

The present invention is concerned with a process for the catalytic hydrogenation of organic compounds on a catalyst of amorphous metal alloys under near-critical or supercritical conditions of the solvent.

2. Description

Amorphous metal alloys are also known in the art as metallic glasses. They can be produced, for example, by the shock cooling of the molten alloy on a cooled, rotating copper wheel. Depending on the nature of the surface of the copper wheel and on the precise process conditions there are obtained thin metal ribbons (in the case of a smooth copper surface) or flake-like particles, so-called flakes, (in the case of a rough copper surface). The thickness of the metal ribbons or of the flakes lies in the range between 5 and 50 $\mu$m, preferably between 10 and 30 $\mu$m, especially about 20 $\mu$m. If the ribbons or flakes were to be made thicker, heat cannot dissipate at a rapid enough rate. Increasing the thickness increases the formation of a crystalline alloy structure.

Metallic glasses obtained in the above process are non-porous. Their surface is therefore formed exclusively by their external geometric surface. This surface area is only about 0.5 $m^2/g$ in the case of the preferred metal ribbons or flakes of 20 $\mu$m thickness. In contrast, activated nickel powder catalysts have specific metal surface areas of more than 100 $m^2/g$ and finely dispersed palladium catalysts carried on active charcoal have specific metal surface areas of more than 40 $m^2/g$.

Although the catalytic properties of metallic glasses have been investigated intensively, because of their small metal surface area, they have never before been used as catalysts for industrial processes. An overview on the state of the art for catalysis on metallic glasses is found in the article "Glassy Metals in Catalysis" by A. Baiker in "Topics in Applied Physics" Vol. 72., pages 121–162, Ed. H. Beck and H.-J. Güntherodt, published by Springer 1994.

Metallic glasses can catalyze a large number of hydrogenation reactions, for example the hydrogenation of nitrogen, ethene or butadiene (see European Patent No. 0 173 088 B1) at temperature in the range of 90° C. to 450° C. and gas pressures of below 10 bar.

Catalytic activity depends on the respective alloy composition of the metallic glass. For example, $Pd_{81}Si_{19}$ glasses have been found to be especially suitable for the selective hydrogenation of alkynes to alkenes [A. Molnar et al.; J. Catal. 101: 67–72 (1986)]. However, these hydrogenations were carried out at room temperature and at atmospheric hydrogen pressure.

In spite of the fundamental suitability of metallic glasses for catalytic hydrogenations, the small metal surface, low thermal stability and the formation of stable oxide layers on the surface of the metallic glasses during their production were seen to be serious obstacles for their use in industrial hydrogenation processes [D. Gasser and A. Baiker, Applied Catalysis, 48: 279–294 (1989)]. Moreover, it was suspected that the action of hydrogen would cause the metallic glasses to become friable, which would finally lead to their pulverization.

Thus, an object of the present invention is to provide an industrial process for the catalytic hydrogenation of organic compounds on metallic glasses, which overcomes the obstacles known from the state of the art for the use of metallic glasses in industrial hydrogenation processes, permits hydrogenations with high space-time yields and good long-term stability of the catalytic activity, and solves the problems associated with the reactant spending too much time on the catalyst.

SUMMARY OF THE INVENTION

The subject invention provides a process for hydrogenating an organic compound, which comprises reacting the organic compound with hydrogen in the presence of an amorphous metal alloy and a solvent, the solvent being under near-critical or super-critical conditions, so as to hydrogenate the organic compound.

DETAILED DESCRIPTION OF THE INVENTION

Figure 1:
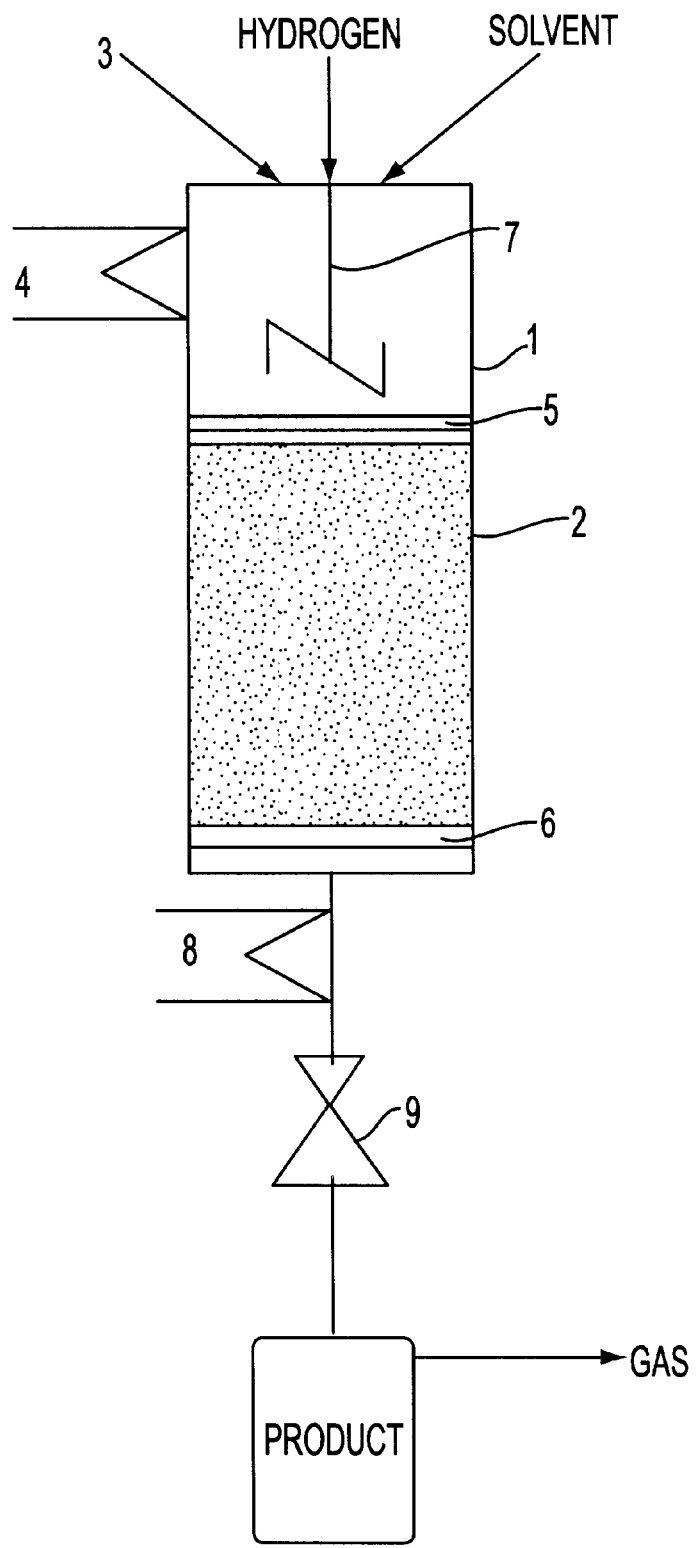
FIG. 1 depicts reactor for the continuous hydrogenation of organic compounds.

The present invention will now be described in terms of its preferred embodiments. These embodiments are set forth to aid in understanding the invention, but are not to be construed as limiting.

Metallic glasses used in accordance with the invention have numerous advantages compared with conventional carrier catalysts or activated metal catalysts. Metallic glasses are non-porous (that is pore-free). Thus, catalyst problems caused by insufficient diffusion velocities in the pores of conventional, porous catalyst systems do not arise. Frequently, diffusion velocity is much less than reaction velocity, which means that the product formed in the catalytic reaction remains much too long on the catalyst. This is of disadvantage when carrying out selective reactions. In the case of pore-free metallic glasses, this problem does not occur.

The quasimetallic heat conductivity of the metallic glasses is a great advantage in both exothermic reactions and endothermic reactions. In the subject process, the use of $Pd_{81}Si_{19}$ leads to a uniform temperature in the reactor bed. In contrast, the use of conventional palladium carrier catalysts can result in overheating in the reactor because of the poor heat conductivity of oxidic carrier materials, for example, aluminium, silicon and titanium oxides. Provision must be made for a better heat conduction to avoid such overheating, for example by stronger dilution of the organic compound with a solvent.

The object of the subject invention is achieved by carrying out the hydrogenation of organic compounds in the presence of metallic glasses (catalysts of amorphous metal alloys) and in a solvent under near-critical or supercritical conditions of the solvent [for a description of the familiar terms "near-critical" and "supercritical" see "Interaction of Density, Viscosity and Interfacial Tension in Countercurrent Extraction with Near-Critical Fluids" in "High Pressure Chemical Engineering", pages 191–197, Ed. Ph. Rudolf von Rohr and Ch. Trepp, Elsevier Science B.V. 1996, and the literature references cited therein]. The subject process is the catalytic hydrogenation of an organic compound on a catalyst of an amorphous metal alloy and in a solvent. This process comprises carrying out the hydrogenation under near-critical or supercritical conditions of the solvent. Such near-critical or super-critical conditions are readily determined by the skilled artisan having read the present specification, but are generally within 5 bar and 10° C. of the solvent's critical condition. For guidance, the term "near" generally encompasses no lower than 5 bar and 10° C. below the critical pressure/temperature of the solvent being used. The terms "near" and "super" reflect a proximity to the critical pressure/temperature of the solvent being used. Such proximity can be readily determined by the skilled artisan for any given solvent.

Preferably, the hydrogenation is carried out at a hydrogen partial pressure between 5 and 400 bar (0.5 and 40 MPa).

The subject reaction temperatures range between room temperature and 300° C. and are therefore similar to those used in corresponding conventional hydrogenations.

Metallic glasses from alloy mixtures having a eutectic melting point are useful catalysts in the subject process. The eutectics can be found from the known phase diagrams of the alloy mixtures. The amorphous structure of the metallic glasses is achieved—as mentioned above—by shock cooling the alloy melts. Alloys of a metal from the group of palladium, iron, copper, nickel and vanadium and a metal from the group of titanium, zirconium, silicon, germanium, niobium, boron, phosphorus, antimony and bismuth are preferred.

It is known that metallic glasses are only obtained in the case of alloy compositions which correspond to the eutectic mixtures of the alloy components or come very close to these eutectic mixtures. Typical compositions of preferred alloys which can be used in the process in accordance with the invention are $Pd_{18}Si_{19}$, $Fe_{24}Zr_{76}$, $Fe_{91}Zr_9$, $Ni_{64}Zr_{36}$, $Ni_{64}Ti_{34}$ and $Fe_{85}B_{15}$. $Pd_{81}Si_{19}$ is the especially preferred amorphous metal alloy which is used. The actual compositions of the alloys used should deviate by at most about 2% (±2%) from these ideal compositions. In the case of greater deviations there is the danger of the metallic glasses having an increasing content of crystalline regions.

In the scope of the present invention it has been found that by increasing the hydrogen partial pressure to values above 5 bar (0.5 MPa) the catalytic activity of the metallic glass can be increased in such a manner that, in spite of the small metallic surface, space-time yields are possible which are equal to or better than the values which are achieved with conventional carrier catalysts having a substantially larger metallic surface. Moreover, it was surprisingly found that the hydrogen embrittlement that was feared in the prior art does not occur. As mentioned above, the hydrogen partial pressure is preferably not more than 400 bar (40 MPa).

For the performance of the process in accordance with the invention, the metallic glasses can be used in the form of ribbons or flakes. However, flakes are preferred. Both flakes and ribbons conveniently have layer thicknesses in the range between about 5 and about 50 μm, preferably between about 10 and about 30 μm, especially about 20 μm. Metal alloys which are sufficiently amorphous are no longer obtained above a thickness of 50 μm because of the insufficiently rapid heat dissipation in the shock cooling. Preferably, flakes with average areas of 0.5 to 30 mm² are used. Such flakes can be produced either directly during the production of the metallic glasses or can be obtained subsequently from ribbons by milling.

In carrying out the subject process, the appropriate solvent depends on the organic compound to be hydrogenated. Useful solvents include aromatic and aliphatic hydrocarbons, such as benzene, toluene, propane or butane; carbon dioxide; alcohols, such as methanol or ethanol; or mixtures thereof.

Supercritical carbon dioxide [critical temperature about 31° C. and critical pressure about 73 bar (7.3 MPa)], optionally in admixture with propane or butane, is preferably used as the solvent in this process. According to German Patent Publication (DOS) 44 05 029 A1, supercritical carbon dioxide has outstanding properties in hydrogenation reactions. It has a good dissolving capacity not only for hydrogen, but also for many organic compounds. In its supercritical state it has a low viscosity at a relatively high density. After passage through the reactor it can generally be separated from the product in a simple manner, without environmental contamination, by decompression and can be recycled.

In other respects, techniques known from conventional processes can be used. Thus, hydrogenations can be carried out in a solid bed reactor, whereby the hydrogen can be used in countercurrent or parallel flow. The subject process is preferably used for continuous hydrogenations.

The subject process can be used in all conventional hydrogenation reactions on organic compounds. Not only non-selective, but also selective hydrogenation reactions can be accomplished with this process. Examples are the selective or complete hydrogenation of the double bonds of fatty acids, the hydrogenation of fatty acids to fatty alcohols, the hydrogenation of sugars, the hydrogenation of halonitroaromatics to haloamines, the ring hydrogenation of aromatic compounds and quite generally the selective hydrogenation of alkynes to alkenes. The process in accordance with the invention is preferably used for the hydrogenation of 3,7,11,15-tetramethyl-1-hexadecyn-3-ol (dehydroisophytol) to 3,7,11,15-tetramethyl-1-hexadecen-3-ol (isophytol).

Not all metallic glasses are equally well suited for all of the enumerated reactions. However, the art of conventional hydrogenation processes can be turned to for guidance. For example, it is known that the metal catalyst iron is appropriate for ammonia production by hydrogenation of nitrogen, nickel is appropriate for hydrogenation of unsaturated fatty acids and palladium is appropriate for the hydrogenation of alkynes to alkenes.

The catalytic activity for a particular reaction depends on the composition of the chosen metal alloy. An indication for the choice of the most suitable metallic glasses is given by the catalysts used in the corresponding conventional hydrogenation process. Thus, for example, the metallic glass having the composition $Pd_{81}Si_{19}$ is very well suited for all hydrogenations in which palladium catalysts are used in accordance with the state of the art. Examples of these are the selective hydrogenations of alkynes to alkenes. As is also known from conventional catalysts, the metallic glasses can be optionally poisoned in order to increase the selectivity. Lead and sulphur compounds, for example, lead acetate or 1,2-bis-(2-hydroxyethylthio)ethane, alone or in combination, are frequently used for this purpose.

Lead compounds are especially suitable for poisoning palladium-containing catalysts used in accordance with the invention for the selective hydrogenation of alkynes to alkenes, and are in general the preferred poisoning compounds for this purpose. The amount of lead (lead atoms, Pb) taken up is correlated with the number of palladium atoms on the surface (Pd): a Pd:Pb atom ratio of about 2:1 has been found to be most appropriate. As is known, the determination of the Pd can be effected using carbon monoxide chemisorption. As an alternative to lead compounds, other transition metal-containing compounds, such as zinc, tin, manganese and copper compounds, as well as compounds with ligand functions to palladium, such as sulphur compounds, for example, sulphides, thiols and dimethyl sulphoxide; amines, for example, pyridine, γ-collidine, quinoline, quinaldine and piperidine; phosphines; and carbon monoxide, can be used to increase the selectivity of palladium for the hydrogenation of alkynes to alkenes. Poisoning sulphur compounds are especially suitable in the selective hydrogenation of dehydroisophytol to isophytol in accordance with the present invention. For example, when 1,2-bis-(2-hydroxyethylthio)ethane is used for this purpose about 0.005 to about 0.1 weight percent of this compound based on the amount of educt is suitably used.

The following Examples were actually performed to illustrate the subject process. FIG. 1 shows a tube reactor suitable for continuous hydrogenation of organic compounds.

EXAMPLE 1

The allene 6,10,14-trimethyl-4,5-pentadecadien-2-one was hydrogenated continuously to 6,10,14-trimethyl-pentadecan-2-one in the tube reactor represented in FIG. 1. The tube reactor consisted of a stainless steel tube 1, which was provided on its internal surface with a 2.5 mm thick polytetrafluoroethylene coating. The free internal diameter of the reactor was 20 mm. 74 g of amorphous $Pd_{81}Si_{19}$ in the form of flakes were filled into the reactor as the catalyst 2. The flakes were obtained by milling the ribbon-like material at the temperature of liquid nitrogen. The average diameter of the flakes was 5 mm, their thickness 20 μm and their heat density 2.5 g/cm³.

The catalyst layer was situated between two frits 5 and 6. A stirrer 7 was arranged at the top of the reactor.

The hydrogenations were carried out at a pressure of 140 bar (14 MPa) using carbon dioxide ($CO_2$) as the solvent. Carbon dioxide was present in the supercritical state under the conditions in the reactor.

Educt 3, hydrogen and carbon dioxide were introduced at the top of the reactor and conducted over the catalyst filling. The reaction mixture was heated above the catalyst filling to the required reaction temperature of 140° to 200° C. using a heating mantle 4. After having passed through the catalyst filling the reaction mixture was cooled in a condenser 8 and the product was separated by decompression 9 from the solvent carbon dioxide and from unconsumed hydrogen.

The product mixture was analyzed by gas chromatography (GC). Table 1 gives the results of these measurements for a continuous hydrogenation over the period of 1630 minutes. In this, 2.04 mol of educt and 21.42 mol of hydrogen were added per hour to the reactor. The space-time yield of the product 6,10,14-trimethyl-pentadecan-2-one was 123 mol per liter per hour (mol/lh).

TABLE 1

| Time [min] | $CO_2$ [g/h] | Temperature [° C.] | Product [GC %] |
|---|---|---|---|
| 0 | 1200 | 192 | 88.9 |
| 50 | 1200 | 192 | 88.9 |
| 140 | 1200 | 192 | 89.2 |
| 225 | 1200 | 192 | 88.9 |
| 280 | 1200 | 192 | 89.0 |
| 340 | 1200 | 181 | 88.0 |
| 395 | 1200 | 181 | 88.1 |
| 445 | 1200 | 181 | 86.8 |
| 480 | 900 | 166 | 87.5 |

TABLE 1-continued

| Time [min] | $CO_2$ [g/h] | Temperature [° C.] | Product [GC %] |
|---|---|---|---|
| 520 | 900 | 166 | 86.0 |
| 565 | 900 | 166 | 86.3 |
| 645 | 900 | 166 | 86.6 |
| 765 | 600 | 166 | 86.1 |
| 885 | 300 | 160 | 88.2 |
| 1005 | 0 | 154 | 88.3 |
| 1125 | 300 | 159 | 87.9 |
| 1245 | 600 | 162 | 85.9 |
| 1365 | 900 | 165 | 84.9 |
| 1505 | 600 | 163 | 87.2 |
| 1545 | 0 | 142 | 88.6 |
| 1585 | 0 | 142 | 88.0 |
| 1630 | 0 | 142 | 89.0 |

EXAMPLE 2

The reactor of Example 1 was used to hydrogenate the alkyne 3,7,11,15-tetramethyl-1-hexadecyn-3-ol (dehydroisophytol) to the alkene 3,7,11,15-tetramethyl-1-hexadecen-3-ol (isophytol). The reactor was filled with 80 g of ground $Pd_{81}Si_{19}$. 1080 g of $CO_2$ were dosed in per hour as the solvent. The reaction pressure was 140 bar (14 MPa).

Table 2 gives the gas-chromatographical analyses of the production mixture as well as the respective space-time yields for the alkane 3,7,11,15-tetramethyl-hexadecan-3-ol likewise formed.

TABLE 2

| Hydrogenation conditions | | | | Analysis of the product mixture | | | |
|---|---|---|---|---|---|---|---|
| Time | $H_2$ | Alkyne | Temp. | Alkyne | Alkene | Alkane | |
| min | mol/h | mol/h | ° C. | GC % | GC % | GC % | STY |
| 67 | 1.8 | 0.36 | 129 | 0.0 | 0.5 | 96.9 | 22 |
| 102 | 1.8 | 0.36 | 129 | 0.0 | 0.4 | 96.8 | 22 |
| 189 | 2.7 | 0.54 | 135 | 0.0 | 0.4 | 96.6 | 33 |
| 202 | 2.7 | 0.54 | 135 | 0.0 | 0.4 | 96.5 | 33 |
| 283 | 3.6 | 0.72 | 141 | 0.0 | 0.3 | 95.9 | 44 |
| 292 | 3.6 | 0.72 | 141 | 0.0 | 0.4 | 96.3 | 44 |
| 361 | 4.5 | 0.90 | 147 | 0.0 | 0.5 | 95.5 | 54 |
| 375 | 4.5 | 0.90 | 147 | 0.0 | 0.3 | 95.1 | 54 |
| 89 | 2.3 | 0.90 | 149 | 0.0 | 0.4 | 95.5 | |
| 109 | 2.3 | 0.90 | 149 | 0.0 | 0.4 | 95.8 | |
| 195 | 1.5 | 0.90 | 149 | 1.3 | 20.8 | 74.7 | |
| 207 | 1.5 | 0.90 | 149 | 1.5 | 22.9 | 72.4 | |
| 265 | 1.1 | 0.90 | 143 | 5.4 | 27.8 | 63.8 | |
| 274 | 1.1 | 0.90 | 143 | 9.8 | 32.9 | 54.5 | |
| 318 | 1.1 | 1.26 | 144 | 22.6 | 33.9 | 41.0 | |
| 327 | 1.1 | 1.26 | 144 | 26.4 | 34.1 | 37.0 | |
| 392 | 1.1 | 1.62 | 145 | 27.2 | 33.5 | 36.9 | |
| 398 | 1.1 | 1.62 | 145 | 27.0 | 33.4 | 37.1 | |
| 430 | 1.1 | 0.90 | 131 | 11.5 | 29.3 | 56.8 | |
| 527 | 1.1 | 0.90 | 131 | 11.3 | 29.9 | 56.2 | |

STY: Space-time yield in mol/lh.

EXAMPLE 3

Dehydroisophytol was hydrogenated selectively to isophytol in the tube reactor previously described (see FIG. 1). For this purpose, the $Pd_{81}Si_{19}$ catalyst was poisoned as follows with a lead compound. The ground, metallic glass was covered for a period of 3 hours at room temperature with a supersaturated solution of lead acetate in ethanol. After pouring off the solution the flakes were dried in a vacuum, thereafter stored for a duration of 3 hours under a hydrogen gas atmosphere and subsequently washed with deionized water and acetone.

For the hydrogenations, 48.3 g of the thus-treated flakes were filled into the reactor. Table 3 gives the reaction conditions and analytical results of the product mixture.

TABLE 3

| Hydrogenation conditions | | | | Analysis of the product mixture | | | |
|---|---|---|---|---|---|---|---|
| Time | CO$_2$ | H$_2$ | Educt | Temp. | Educt | Alkene | | Alkane |
| min | g/h | mol/h | mol/h | °C. | GC % | GC % | STY | GC % |
| 80 | 1200 | 3.2 | 1.6 | 84 | 0.0 | 87.9 | 75 | 9.8 |
| 195 | 1200 | 3.0 | 1.6 | 84 | 0.0 | 90.2 | 75 | 6.7 |
| 330 | 1200 | 2.8 | 1.6 | 84 | 0.0 | 90.9 | 75 | 6.2 |
| 430 | 1200 | 2.7 | 1.6 | 84 | 0.0 | 90.8 | 75 | 6.1 |
| 480 | 1200 | 2.5 | 1.6 | 83 | 0.0 | 91.1 | 75 | 6.2 |
| 95 | 1200 | 3.2 | 1.6 | 79 | 0.2 | 90.9 | 75 | 6.7 |
| 220 | 1200 | 3.0 | 1.6 | 78 | 0.2 | 91.2 | 75 | 6.5 |
| 360 | 1200 | 2.8 | 1.6 | 78 | 0.5 | 91.0 | 75 | 5.8 |
| 430 | 1200 | 2.7 | 1.6 | 77 | 0.8 | 90.9 | 75 | 5.9 |
| 480 | 1200 | 2.5 | 1.6 | 74 | 4.2 | 88.6 | 75 | 5.3 |
| 90 | 840 | 2.8 | 1.6 | 97 | 0.5 | 87.8 | 75 | 9.5 |
| 200 | 840 | 2.7 | 1.6 | 97 | 0.0 | 89.5 | 75 | 8.2 |
| 305 | 840 | 2.5 | 1.6 | 96 | 0.0 | 90.3 | 75 | 8.6 |
| 400 | 840 | 2.4 | 1.6 | 97 | 0.0 | 90.7 | 75 | 7.0 |
| 470 | 840 | 2.3 | 1.6 | 96 | 0.4 | 91.1 | 75 | 7.1 |
| 235 | 840 | 2.7 | 1.6 | 95 | 0.7 | 89.3 | 75 | 8.1 |
| 325 | 840 | 2.7 | 1.5 | 91 | 0.3 | 99.5 | 70 | 7.2 |
| 415 | 840 | 2.7 | 1.4 | 88 | 0.1 | 91.1 | 65 | 6.8 |
| 475 | 840 | 2.7 | 1.3 | 84 | 0.1 | 90.3 | 60 | 7.6 |

STY: Space-time yield in mol/l/h.

EXAMPLE 4

To increase the selectivity of the hydrogenation of Example 3 further, Pd$_{81}$Si$_{19}$ alloy poisoned with lead was again used as the catalyst. In addition, the catalyst was poisoned with a sulphur compound. For this purpose, 1,2-bis-(2-hydroxyethylthio)ethane was dosed into the educt mixture. The precise experimental conditions and results are set forth in Table 4; this is thus a comparison with a hydrogenation on a palladium carrier catalyst.

COMPARATIVE EXAMPLE

Analogously to Example 4, dehydroisophytol was hydrogenated to isophytol on a conventional palladium carrier catalyst. The catalyst contained 4 wt. % palladium as well as 4 wt. % lead on a carrier of an organofunctional polysiloxane. This catalyst is described in German Patent No. 41 10 706. The experimental conditions and results will be evident from Table 4.

TABLE 4

Continuous hydrogenation of dehydroisophytol to isophytol

| | | Example 4 | Comparative Example |
|---|---|---|---|
| Catalyst | | Pd$_{81}$Si$_{19}$ | 4 wt. % Pd + 4 wt. % Pb |
| Catalyst amount | [g] | 44 | 34 |
| Catalyst volume | [cm$^3$] | 20 | 120 |
| Pd-effective area | [m$^2$] | 0.5 | 40 |
| Educt/dosage + 1 wt. % sulphur cpd. | [g/h] | 460 | 430 |
| CO$_2$ | [g/h] | 660 | 1980 |
| H$_2$-pressure | [bar] | 140 | 140 |
| Temperature | [°C.] | 110 | 110 |
| Yield | [%] | | |
| Space-time yield | [kg/lh] | 23 | 4 |

The subject invention has been described above in terms of its preferred embodiments. Upon reading this specification, numerous alternative embodiments will become obvious to the skilled artisan. These embodiments are to be considered within the scope and spirit of the subject invention which is only to be limited by the claims that follow and their equivalents.

What is claimed is:

1. A process for hydrogenating an organic compound, which comprises reacting the organic compound with hydrogen in the presence of an amorphous metal alloy and a solvent, the solvent being under near-critical or super-critical conditions, so as to hydrogenate the organic compound.

2. The process according to claim 1, wherein the reacting is performed at a hydrogen partial pressure between 5 and 400 bar.

3. The process according to claim 1, wherein the reacting is in the presence of an amorphous metal alloy selected from the group consisting of palladium, iron, copper, nickel and vanadium and a metal from the group of titanium, zirconium, silicon, germanium, niobium, boron, phosphorus, antimony, and bismuth.

4. The process according to claim 3, wherein the reacting is in the presence of an amorphous metal alloy which is Pd$_{81}$Si$_{19}$, Fe$_{24}$Zr$_{76}$, Fe$_{91}$Zr$_9$, Ni$_{64}$Zr$_{36}$, Ni$_{64}$Ti$_{34}$ or Fe$_{85}$B$_{15}$.

5. The process according to claim 4, wherein the reacting is in the presence of an amorphous metal alloy which is Pd$_{81}$Si$_{19}$.

6. The process according to claim 1, wherein the reacting is in the presence of an amorphous metal alloy which is in the form of ribbons or flakes having a layer thickness in the range between about 5 μm and about 50 μm.

7. The process according to claim 6, wherein the reacting is in the presence of an amorphous metal alloy which is in the form of ribbons or flakes having a layer thickness in the range between about 10 μm and about 30 μm.

8. The process according to claim 7, wherein the reacting is in the presence of an amorphous metal alloy which is in the form of ribbons or flakes having a layer thickness about 20 μm.

9. The process according to claim 1, wherein the reacting is in the presence of an amorphous metal alloy which is in the form of flakes having an average surface area of from about 0.5 mm$^2$ to about 30 mm$^2$.

10. The process according to claim 1, wherein the reacting is in the presence of an amorphous metal alloy which is poisoned with a lead compound, a sulphur compound, or a combination thereof.

11. The process according to claim 1, wherein reacting is in the presence of a solvent which is an aromatic hydrocarbon, an aliphatic hydrocarbon, carbon dioxide, an alcohol, or a mixture thereof.

12. The process according to claim 11, wherein the reacting is in the presence of a solvent which is an aromatic hydrocarbon.

13. The process according to claim 12, wherein the reacting is in the presence of a solvent which is benzene or toluene.

14. The process according to claim 11, wherein the reacting is in the presence of a solvent which is an aliphatic hydrocarbon.

15. The process according to claim 14, wherein the reacting is in the presence of a solvent which is propane or butane.

16. The process according to claim 11, wherein the reacting is in the presence of a solvent which is carbon dioxide.

17. The process according to claim 16, wherein the reacting is in the presence of a solvent which is super-critical carbon dioxide.

18. The process according to claim 11, wherein the reacting is in the presence of a solvent which is an alcohol.

19. The process according to claim 18, wherein the reacting is in the presence of a solvent which is methanol or ethanol.

20. The process according to claim 1, wherein the reacting is carried out on a continuous basis.

21. The process according to claim 1, wherein the reacting involves an organic compound which is 3,7,11,15-tetramethyl-1-hexadecyn-3-ol (dehydroisophytol) and this organic compound is hydrogenated to 3,7,11,15-tetramethyl-1-hexadecen-3-ol (isophytol).

* * * * *